United States Patent
Baillet (10) Patent No.: US 11,045,616 B2
(45) Date of Patent: Jun. 29, 2021

(54) DEVICE FOR DISTRIBUTION OF FLUID PRODUCT TRIGGERED BY INHALATION

(71) Applicant: APTAR FRANCE SAS, Le Neubourg (FR)

(72) Inventor: Matthieu Baillet, Rouen (FR)

(73) Assignee: APTAR FRANCE SAS, Le Neubourg (FR)

( * ) Notice: Subject to any disclaimer, the term of this patent is extended or adjusted under 35 U.S.C. 154(b) by 692 days.

(21) Appl. No.: 15/525,345

(22) PCT Filed: Nov. 17, 2015

(86) PCT No.: PCT/FR2015/053096
§ 371 (c)(1),
(2) Date: May 9, 2017

(87) PCT Pub. No.: WO2016/079410
PCT Pub. Date: May 26, 2016

(65) Prior Publication Data
US 2017/0319798 A1 Nov. 9, 2017

(30) Foreign Application Priority Data

Nov. 21, 2014 (FR) ..................................... 1461291

(51) Int. Cl.
*A61M 15/00* (2006.01)
*B65D 83/44* (2006.01)

(52) U.S. Cl.
CPC ...... *A61M 15/0091* (2013.01); *A61M 15/009* (2013.01); *A61M 15/0065* (2013.01); *A61M 15/0026* (2014.02); *B65D 83/44* (2013.01)

(58) Field of Classification Search
CPC .......... A61M 15/0026; A61M 15/0065; A61M 15/009; A61M 15/0091; A61M 15/0001; B65D 83/44
See application file for complete search history.

(56) References Cited

U.S. PATENT DOCUMENTS

| 3,157,179 A | 11/1964 | Paullus et al. |
| 4,817,822 A * | 4/1989 | Rand .................. A61M 15/009 222/38 |

(Continued)

FOREIGN PATENT DOCUMENTS

| GB | 2 461 153 A | 12/2009 |
| WO | 98/41254 A1 | 9/1998 |

(Continued)

OTHER PUBLICATIONS

International Search Report of PCT/FR2015/053096 dated Feb. 11, 2016 [PCT/ISA/210].

(Continued)

*Primary Examiner* — Victoria Murphy
(74) *Attorney, Agent, or Firm* — Sughrue Mion, PLLC (57) ABSTRACT

A fluid dispenser device having a reservoir; a valve; a cocking member movable between rest and primed positions and between primed and dispensing positions, the cocking member includes a set of teeth; a blocking device blocking the cocking member in the primed position; a trigger system controlled by inhaling to release the blocking device; a reservoir support element including a cam opening; and a meshing wheel having a toothed projection co-operating with the set of teeth and a cam projection co-operating with the cam opening. The toothed projection is centered relative to the wheel rotation axis, and the cam projection is offset relative to the axis. The meshing wheel completes a turn when the cocking member moves from its primed towards its dispensing position, such that the cam projection causes the reservoir support element to perform reciprocating axial movement for actuating and returning the valve into its rest position.

9 Claims, 7 Drawing Sheets

(56) References Cited

U.S. PATENT DOCUMENTS

| | | | | |
|---|---|---|---|---|
| 5,855,564 A * | 1/1999 | Ruskewicz | ....... | A61M 15/0045 |
| | | | | 128/200.14 |
| 2004/0237961 A1 * | 12/2004 | Snow | ................ | A61M 15/0091 |
| | | | | 128/200.23 |
| 2010/0307493 A1 * | 12/2010 | Kirniak | ............. | A61M 15/0045 |
| | | | | 128/203.15 |

FOREIGN PATENT DOCUMENTS

| | | |
|---|---|---|
| WO | 99/44662 A1 | 9/1999 |
| WO | 2013/175121 A1 | 11/2013 |
| WO | 2013/178951 A1 | 12/2013 |

OTHER PUBLICATIONS

International Preliminary Report on Patentability dated Jun. 1, 2017 issued by the International Bureau in PCT/FR2015/053096.

* cited by examiner

DEVICE FOR DISTRIBUTION OF FLUID PRODUCT TRIGGERED BY INHALATION

CROSS REFERENCE TO RELATED APPLICATIONS

This application is a National Stage of International Application No. PCT/FR2015/053096, filed Nov. 17, 2015, claiming priority based on French Patent Application No. 1461291, filed Nov. 21, 2014, the contents of all of which are incorporated herein by reference in their entirety.

The present invention relates to a fluid dispenser device triggered by inhaling, and more particularly to a breath actuated inhaler device of the aerosol type.

Breath actuated inhaler (BAI) devices are well known in the state of the art. The main advantage of this type of device is that fluid dispensing is synchronized with the patient inhaling, so as to guarantee proper dispensing of the fluid. Thus, in the field of aerosol devices, i.e. devices in which the fluid is dispensed by means of a propellant gas, numerous types of breath actuated inhaler device have been proposed. However, those devices present the drawback of including a large number of parts, i.e. they are complicated and costly to manufacture and to assemble, which is obviously disadvantageous. It is also difficult to find the right balance between reliable triggering on each inhalation, without the actuation threshold being too high, and a latch that is robust enough to prevent accidental of unwanted actuation.

Documents U.S. Pat. No. 3,157,179, WO 99/44662, and GB 2 461 153 describe prior-art devices of this type.

An object of the present invention is to provide a breath actuated inhaler device that does not have the above-mentioned drawbacks.

Another object of the present invention is to provide a breath actuated inhaler device that improves operational reliability by guaranteeing actuation on each inhalation.

Another object of the present invention is to provide a breath actuated inhaler device that minimizes the risks of accidental or unwanted actuation.

Another object of the present invention is to provide a breath actuated inhaler device that does not present an actuation threshold that is too high, thereby making it possible for relatively weak people, such as sick or elderly people, to use the device in safe and reliable manner.

Another object of the present invention is to provide a breath actuated inhaler device that is simple and inexpensive to manufacture and to assemble.

The present invention thus provides a fluid dispenser device triggered by inhaling, comprising a fluid reservoir containing a fluid and a propellant gas, a metering valve being assembled on said reservoir for selectively dispensing the fluid, said device further comprising:
  a cocking member that is movable firstly between a rest position and a primed position by compressing a spring, and that is axially movable secondly between said primed position and a dispensing position under the effect of the force exerted by said compressed spring;
  blocking means for blocking said cocking member in said primed position; and
  a trigger system that is controlled by inhaling so as to release said blocking means;
  said cocking member including a set of teeth, and the device further comprising:
  a reservoir support element that is fastened to said reservoir and that includes a cam opening; and
  a meshing wheel comprising firstly a toothed projection that is adapted to co-operate with said set of teeth of said cocking member, and secondly a cam projection that is adapted to co-operate with said cam opening of said reservoir support element, said toothed projection being substantially centered relative to the axis of rotation of said meshing wheel, and said cam projection being offset relative to said axis of rotation, said meshing wheel co-operating with said cocking member so that when said cocking member moves from its primed position towards its dispensing position, said meshing wheel performs a complete turn, such that said cam projection performs a circular movement causing said reservoir support element to perform reciprocating axial movement, with a first axial movement for actuating said valve and a second axial movement in the opposite direction for returning the valve into its rest position.

Advantageously, the device further comprises an actuator member that co-operates with said cocking member, said actuator member being provided with a cam surface for moving said cocking member from a rest position towards a primed position, said actuator member co-operating in said primed position with said blocking means so as to hold said cocking member in said primed position until inhalation, and said actuator member being moved by said cocking member towards a dispensing position after said blocking means have been released so as to actuate said valve.

Advantageously, said blocking means include a latch that, in its blocking position, co-operates with a projection of said actuator member.

Advantageously, said trigger system controlled by inhaling comprises a deformable air chamber that is deformed during inhaling, said deformable air chamber being fastened to a trigger element, such as a pivot rod.

Advantageously, said blocking means are secured to said trigger element.

Advantageously, said reservoir support element co-operates with a support plate that is secured to said body.

Advantageously, said support plate includes holding elements that are adapted to co-operate with holding ramps of said reservoir support element.

Advantageously, said support plate includes rectilinear guide splines that are adapted to co-operate with guide pins of said reservoir support element.

These characteristics and advantages and others appear more clearly from the following detailed description, given by way of non-limiting examples, and with reference to the accompanying drawings, and in which.

Figure 1A:
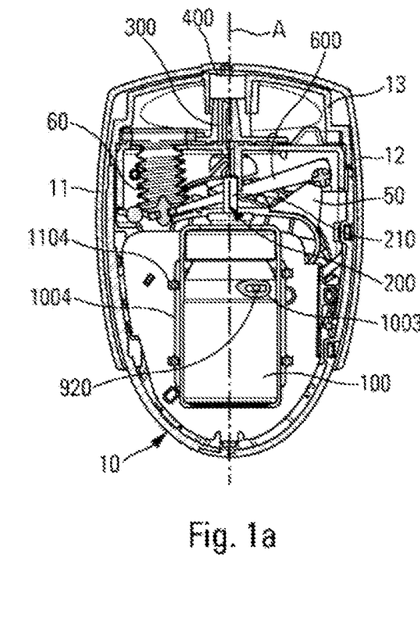
FIGS. 1a and 1b are two partially cut-away diagrammatic views of a breath actuated inhaler device, in an advantageous embodiment of the present invention, shown in its rest position.

In the description, the terms "top" and "bottom" refer to the position shown in particular in FIG. 1a. The term "axial" refers to the vertical central axis A shown in FIG. 1a.

The invention applies more particularly to inhaler devices of the aerosol-valve type for oral dispensing, as described in greater detail below, but it could also apply to other types of inhaler devices, e.g. of the nasal type.

The figures show an advantageous embodiment of the invention, but naturally one or more of the component parts described below could be made in some other way, while providing functions that are similar or identical.

With reference to the drawings, the inhaler device includes a main body 10 on which there can be slidably mounted two cover elements 11, 12 that are adapted to be opened so as to open and prime the device. The main body 10 can be approximately rounded in shape, as shown in the figures, but it could be of any other appropriate shape. An upper body 13 is assembled to the main body 10, forming a mouthpiece 400. The mouthpiece 400 defines a dispenser orifice through which the user inhales while the device is being actuated. The dispenser orifice is typically arranged approximately in the center of the mouthpiece 400. The cover elements 11, 12 can open by pivoting about a common pivot axis, or about two parallel axes by being meshed together. Any other opening means for opening the device can be envisaged. In a variant, the device could include only a single cover element instead of two.

The body 10 contains a reservoir 100 that contains the fluid to be dispensed and a propellant gas, such as a gas of the hydrofluoroalkane (HFA) type, a metering valve 200 being mounted on said reservoir 100 for selectively dispensing the fluid. The metering valve 200 includes a valve member 210 that is axially movable relative to said reservoir 100 during actuation. The metering valve 200 can be of any appropriate type. Advantageously, the valve member 210 is stationary relative to the body 10, and it is the reservoir 100 that is moved axially relative to the body 10 during actuation. The outlet orifice of the valve member 210 of said metering valve 200 is connected via a channel 300 to the dispenser orifice of the mouthpiece 400 through which the user inhales the fluid to be dispensed. Naturally, the dispenser orifice can be made in any way as a function of the desired application of the device. The present description is made with reference to an inhaler including a mouthpiece 400, but it is clear that the invention also applies to other types of uses, such as a nasal inhaler, for example.

Figure 3:
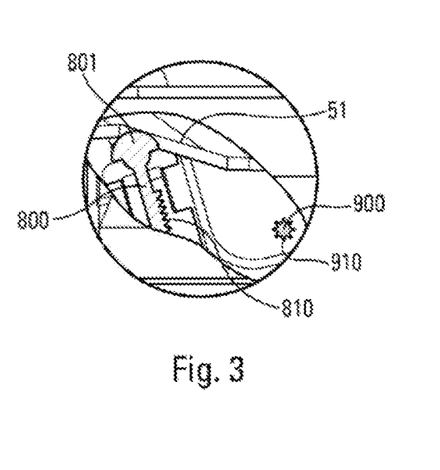
FIG. 3 is a view of a detail of FIG. 1b showing the cocking system in said rest position.
Figure 8:
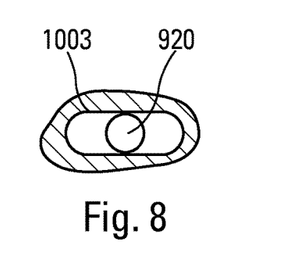
FIG. 8 is a view of a detail of the pin of the meshing wheel in the cam of the reservoir support, in said cocked and non-triggered position.
Figure 9A:
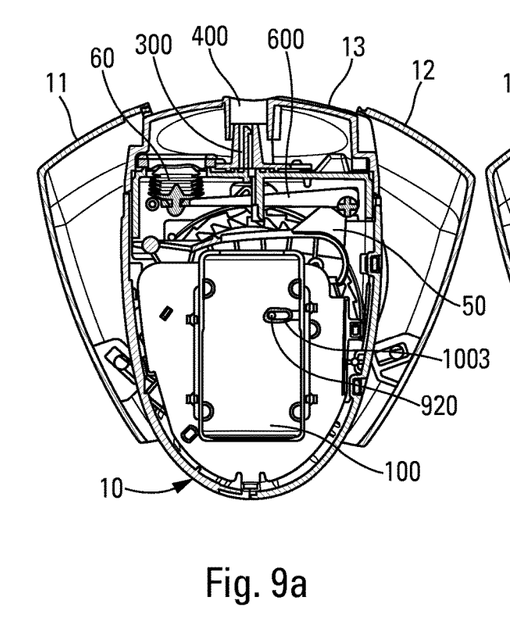
FIGS. 9a and 9b are two views similar to the views in FIGS. 4a and 4b, in the triggered position, after one-fourth of the axial stroke of the slider.
Figure 9B:
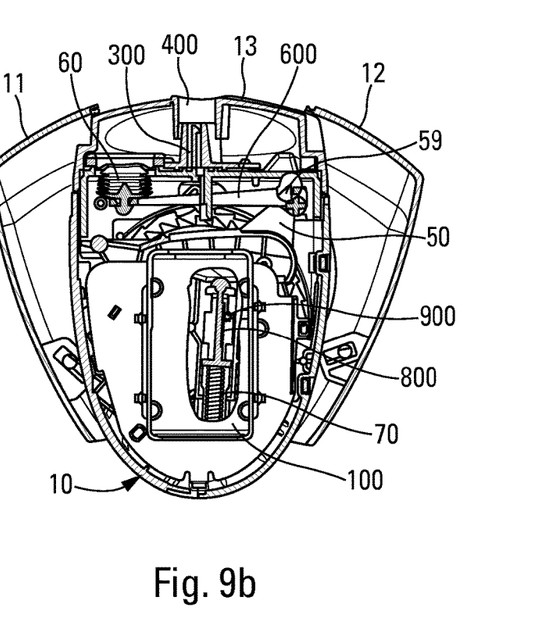
Figure 10:
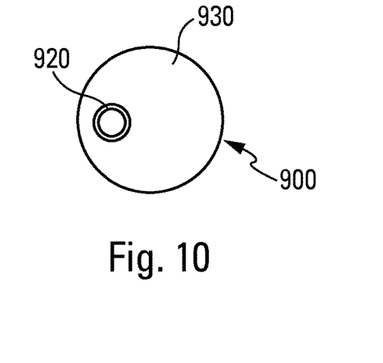
FIG. 10 is a view similar to the view in FIG. 7, in said triggered position, after one-fourth of the axial stroke of the slider.
Figure 11:
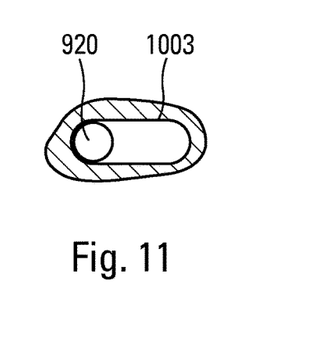
FIG. 11 is a view similar to the view in FIG. 8, in said triggered position, after one-fourth of the axial stroke of the slider.
Figure 12A:
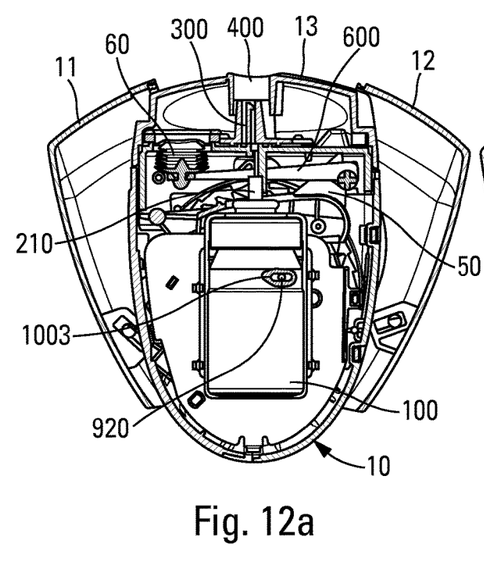
FIGS. 12a and 12b are two views similar to the views in FIGS. 9a and 9b, in the triggered position, after half of the axial stroke of the slider.
Figure 12B:
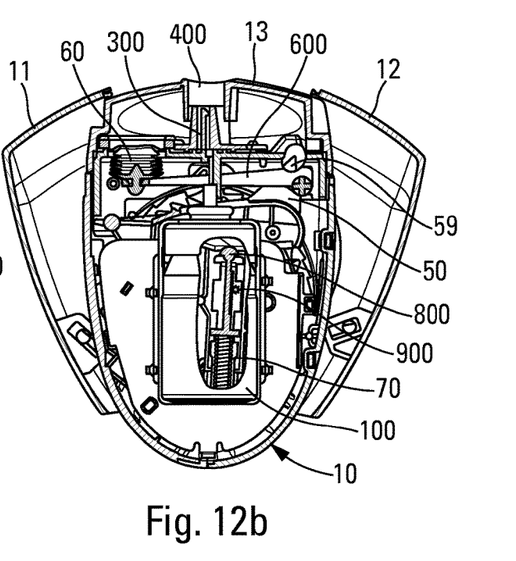
Figure 13:
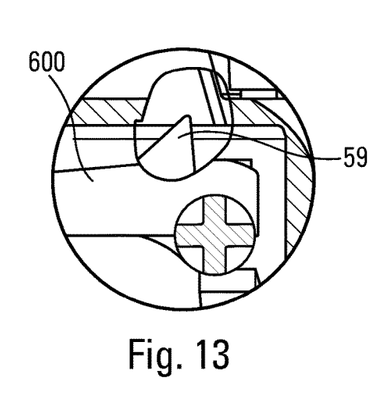
FIG. 13 is a view similar to the view in FIG. 5, in said triggered position, after half of the axial stroke of the slider.
Figure 14:
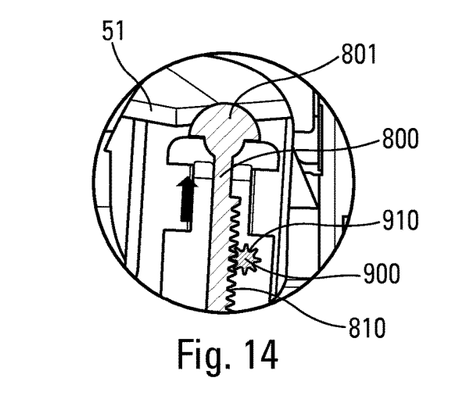
FIG. 14 is a view similar to the view in FIG. 6, in said triggered position, after half of the axial stroke of the slider.
Figure 15:
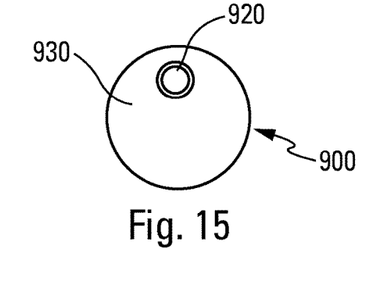
FIG. 15 is a view similar to the view in FIG. 10, in said triggered position, after half of the axial stroke of the slider.
Figure 16:
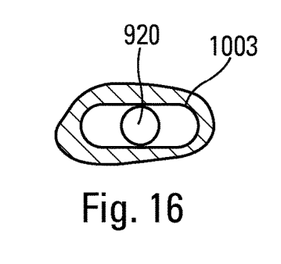
FIG. 16 is a view similar to the view in FIG. 11, in said triggered position, after half of the axial stroke of the slider.
Figure 17A:
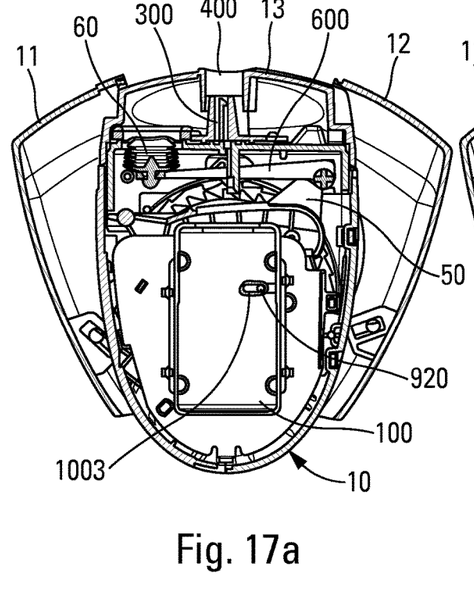
FIGS. 17a and 17b are two views similar to the views in FIGS. 12a and 12b, in the triggered position, after three-fourths of the axial stroke of the slider.
Figure 17B:
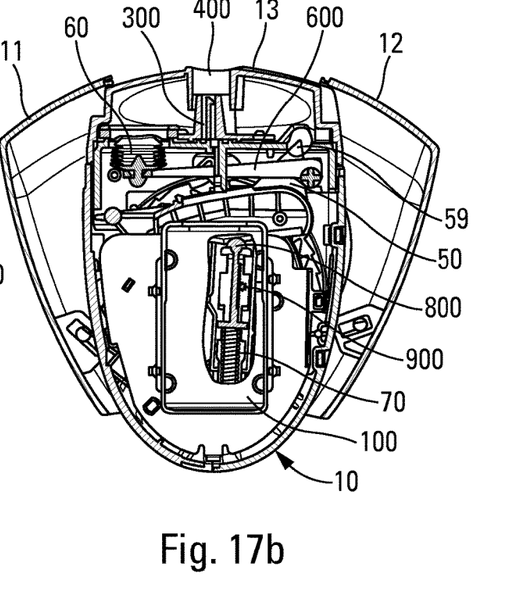
Figure 18:
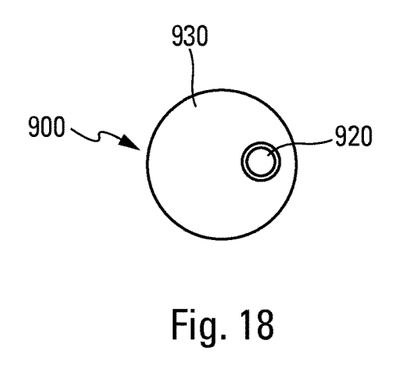
FIG. 18 is a view similar to the view in FIG. 15, in said triggered position, after three-fourths of the axial stroke of the slider.
Figure 19:
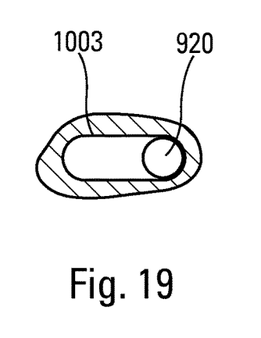
FIG. 19 is a view similar to the view in FIG. 16, in said triggered position, after three-fourths of the axial stroke of the slider.
Figure 20A:
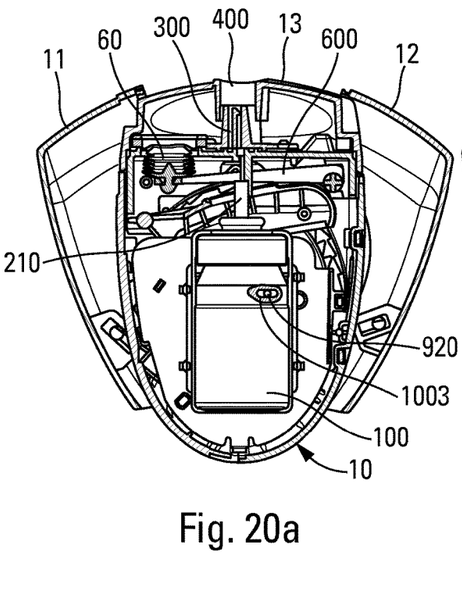
FIGS. 20a and 20b are two views similar to the views in FIGS. 17a and 17b, in the triggered position, after the complete axial stroke of the slider.
Figure 20B:
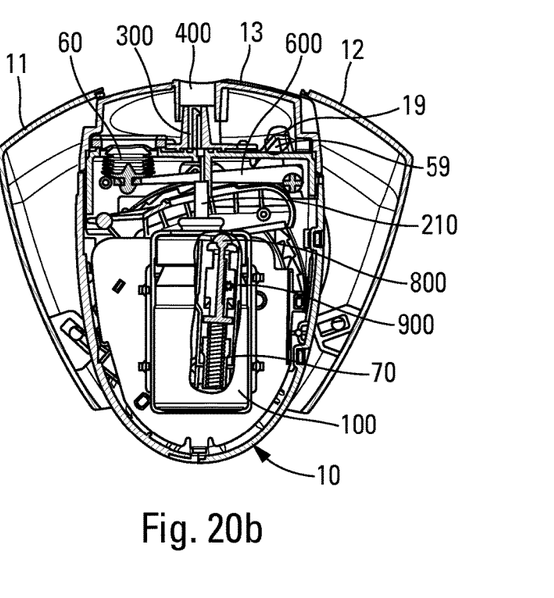

The device includes a primer system. The primer system includes a cocking member 800. The cocking member 800 is secured to at least one of the cover elements 11, 12. The cocking member 800 can move against a spring 70, advantageously a coil spring, initially between a rest position shown in FIG. 3, and a primed position shown in FIG. 8 and then between said primed position and a dispensing position in which it terminates its actuation stroke. FIGS. 20a, 20b, 21, 22, 23, and 24 show this dispensing position. At one end the cocking member 800 is connected to said spring 70, and at its other end it co-operates with an actuator member 50 that is mounted to move, in particular to pivot, on the body 10, initially between a rest position and a primed position, then between said primed position and a dispensing position. The rest position, the primed position, and the dispensing position of the actuator member 50 correspond respectively to the rest position, to the primed position, and to the dispensing position of the cocking member 800.

The cocking member 800 includes a set of teeth 810 that preferably extends axially over one end of said cocking member 800.

Figure 1B:
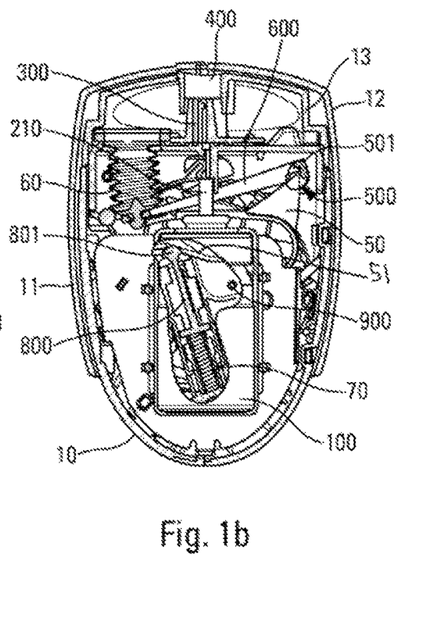
Figure 4A:
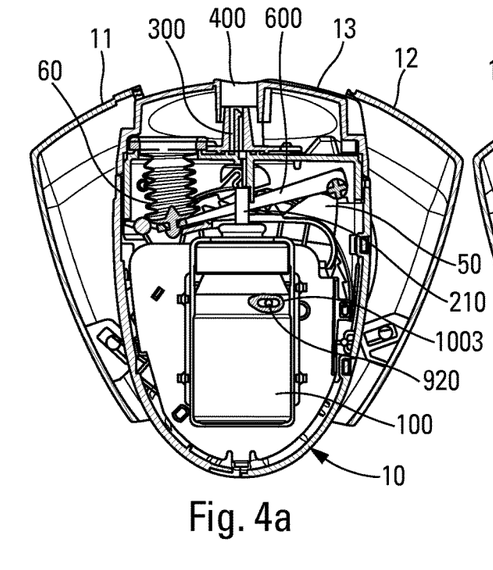
FIGS. 4a and 4b are two views similar to the views in FIGS. 1a and 1b, in the cocked and non-triggered position.
Figure 4B:
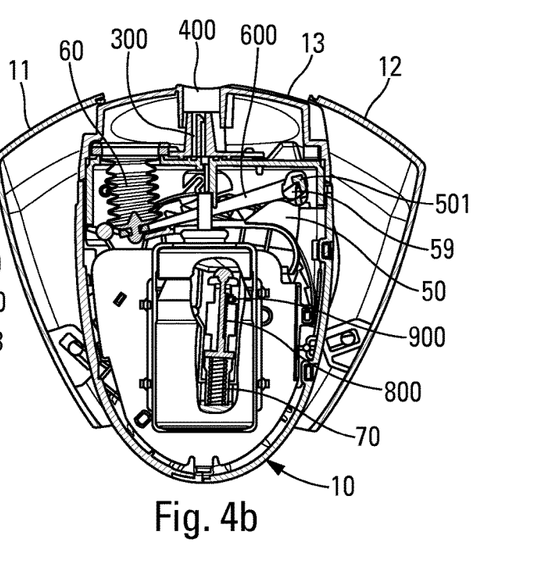

When the cover elements 11, 12 are opened, the cocking member 800 is moved from its rest position towards its primed position, while compressing the spring 70. While moving towards its primed position, the cocking member 800 not only moves along its longitudinal axis so as to compress said spring 70, but it also pivots relative to the body 10, as shown in FIGS. 1b and 4b. Simultaneously, the actuator member 50 is also moved from its rest position towards its primed position. In its primed position, the actuator member 50 is prevented from moving by the blocking means 500 that are released only at the moment of inhaling. Thus, in the absence of any inhaling while in the open position, closing the cover elements 11, 12 merely causes the cocking member 800 and the actuator member 50 to return to the rest position, and the spring 70 to decompress. There is thus no risk of an active dose of fluid being lost by accidental or incomplete actuation in which the user does not inhale between opening and closing the cover elements 11, 12. Thus, the valve 200 can only be actuated and a dose of fluid expelled only when the user inhales.

Figure 2:
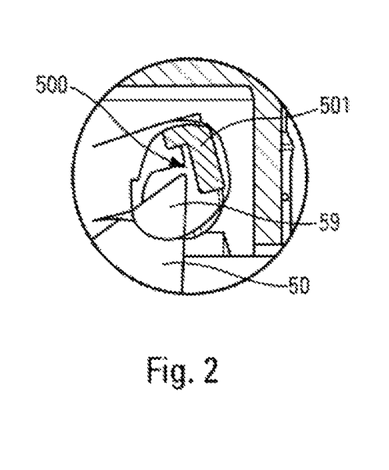
FIG. 2 is a view of a detail of FIG. 1b showing the locking latch in said rest position.
Figure 5:
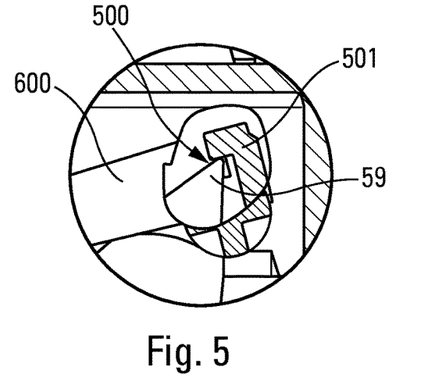
FIG. 5 is a view similar to the view in FIG. 2, in said cocked and non-triggered position.
Figure 6:
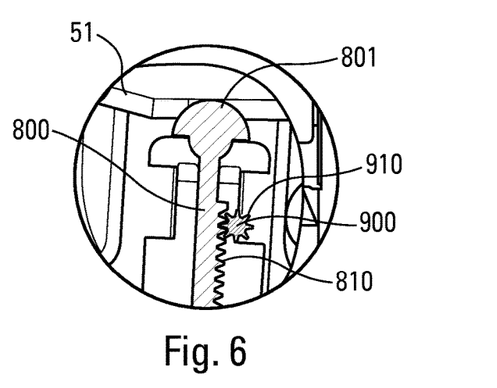
FIG. 6 is a view similar to the view in FIG. 3, in said cocked and non-triggered position.
Figure 7:
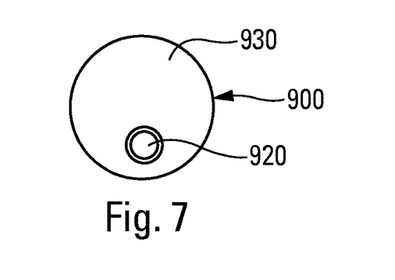
FIG. 7 is a view of a detail of the meshing wheel, in said cocked and non-triggered position.

The blocking means 500 include a latch 501 that is L-shaped and that is adapted to receive a projection 59 of the actuator member 50 in its blocking position. The latch 501 is advantageously secured to, in particular integral with, a trigger element 600. The trigger element 600, e.g. made in the form of a rod, is movable, in particular pivotable, relative to the body 10. The movement or pivoting of said trigger element 600 thus makes it possible to release said blocking means 500 by moving said latch 501 relative to said projection 59 of the actuator member 50. Preferably, in the rest position, said blocking means are not in contact with said actuator member 50, as can be seen in FIG. 2. It is only in the primed position, shown in FIG. 5, that the latch 501 of the blocking means 500 co-operates with said actuator member 50 so as to block it and prevent the valve 200 from being actuated.

A cam surface 51 is formed on said actuator member 50, on which the cocking member 800 slides. Advantageously, in its portion in contact with the cam surface 51, the cocking member 800 includes a rounded portion 801 for facilitating sliding of the cocking member 800 on said cam surface 51. The cam surface 51 comprises at least two cam portions with slopes that are different. A first primer portion, that typically slopes relative to the axis A in FIG. 1a, is provided so as to move the cocking member 800 towards its primed position by compressing the spring 70. A second end portion, that is typically approximately transverse to said axis A, is provided so as to hold the cocking member 800 in its primed position, and so as to co-operate therewith when it moves from its primed position towards its dispensing position.

In the dispensing position, the actuator member 50 has thus been moved upwards (in the orientation in the figures) by the cocking member 800 under the effect of said compressed spring 70.

The device includes a trigger system that is controlled by the user inhaling, and that is for actuating the metering valve 200 when the user inhales through the mouthpiece 400.

The system comprises an air chamber 60 that is deformable under the effect of inhaling, the air chamber 60 being adapted to release said blocking means 500. The user inhaling causes said deformable air chamber 60 to deform, thereby enabling said blocking means 500 to be released, and thus enabling the valve 200 to be actuated.

Advantageously, the air chamber 60 comprises a deformable membrane, such as a bellows, a pouch, or a diaphragm, that can be connected firstly to the mouthpiece 400, and secondly to said blocking means 500 in direct or indirect manner. Thus, during inhalation, the air chamber 60 deforms and/or contracts, thereby causing said blocking means 500 to move into an unblocking position.

Advantageously, the deformable air chamber 60 is connected to said trigger element 600 that supports the blocking means 500 that block the actuator member 50. Thus, while the user is inhaling, said deformable air chamber 60 deforms, causing the trigger element 600 to pivot, thereby releasing said blocking means 500. This enables said actuator member 50 to move towards its dispensing position under the effect of the force exerted by the compressed spring 70 on the cocking member 800. Such movement causes the valve 200 to be actuated and a dose to be dispensed.

The valve 200 is thus actuated only at the moment of inhaling, such that the dose of fluid is expelled out of the dispenser orifice simultaneously with inhaling.

Figure 25:
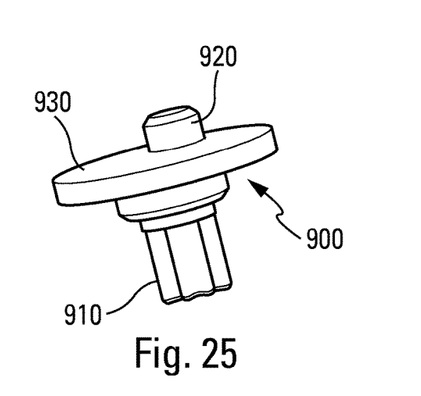
FIG. 25 is a diagrammatic side view of the meshing wheel, in an advantageous embodiment of the present invention.
Figure 26:
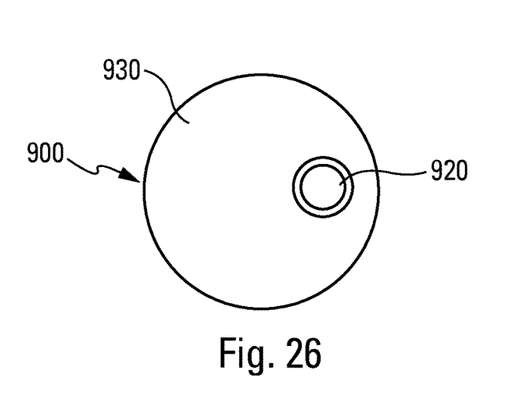
FIG. 26 is a diagrammatic plan view of the FIG. 25 meshing wheel.

The device includes a meshing wheel 900, as can be seen in FIGS. 25 and 26 in particular. The meshing wheel 900 includes firstly a toothed projection 910 that is adapted to co-operate with said set of teeth 810 of said cocking member 800, and secondly a cam projection 920 that is adapted to co-operate with said reservoir 100 or with a portion that is secured thereto. The toothed projection 910 is substantially centered relative to the axis of rotation of said meshing wheel 900, while the cam projection 920 is offset relative to this axis of rotation, while extending in a direction that is parallel to the direction of said toothed projection 910. As can be seen in FIG. 25, the toothed projection 910 extends from one side of a disk 930, while said cam projection 920 extends from the other side of said disk 930. The set of teeth of the toothed projection 910 and the set of teeth 810 of the cocking member 800 are made so that a complete axial actuation stroke of said cocking member 800 corresponds to a complete turn of said meshing wheel 900.

Figure 27:
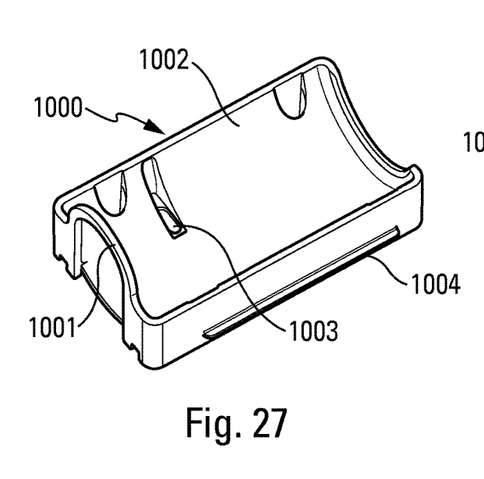
FIG. 27 is a diagrammatic plan view of the reservoir support, in an advantageous embodiment of the present invention.
Figure 28:
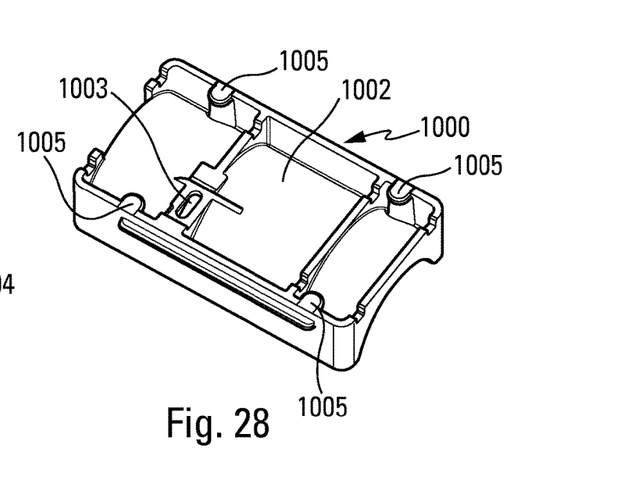
FIG. 28 is a diagrammatic view from below of the FIG. 27 reservoir support.

The device further includes a reservoir support element 1000 in which the reservoir 100 is fastened. The support element 1000 may comprise a bottom wall 1001, and a semi-cylindrical wall 1002 for receiving and holding said reservoir 100, as can be seen in FIGS. 27 and 28 in particular. The semi-cylindrical wall 1002 includes a cam opening 1003 of shape that is oblong or elongate, and holding ramps 1004 and guide pins 1005 on each side of said semi-cylindrical wall 1002. Said cam opening 1003 receives said cam projection 920 of said meshing wheel 900.

Figure 29:
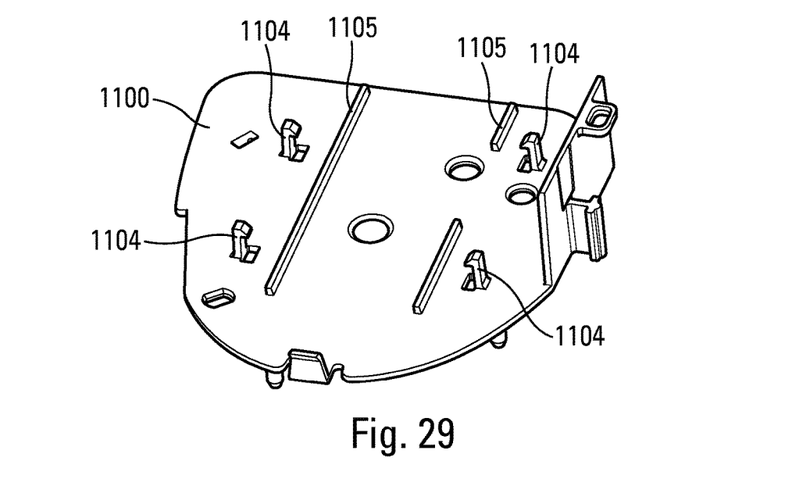
FIG. 29 is a diagrammatic plan view of the guide plate, in an advantageous embodiment of the present invention.

Advantageously, the device also includes a support plate 1100 that is secured to the body 10, i.e. that is not movable relative to said body. The support plate 1100 co-operates with said reservoir support element 1000, the reservoir support element being movable in translation relative to said support plate 1100. As can be seen in FIG. 29, said support plate 1100 includes holding elements 1104 that are adapted to co-operate with said holding ramps 1004 of said reservoir support element 1000, and rectilinear guide splines 1105 that are adapted to co-operate with said guide pins 1005 of said reservoir support element 1000.

When it is desired to use the device, the user opens the cover elements 11, 12, thereby causing the primer system to be actuated. The cocking member 800 moves towards its primed position, thereby causing the spring 70 to compress and thus exert an axial force on the actuator member 50 so as to urge the actuator member towards its dispensing position. While the cocking member 800 is moving towards its primed position, the actuator member 50 is moved so as to come into contact with the latch 501 of the blocking means 500, so that in its primed position the actuator member 50 is held and prevented from moving at all towards its dispensing position. Simultaneously, the set of teeth 810 of the cocking member 800 meshes with the toothed projection 910 of said meshing wheel 900. Thus, during this priming stage, there is no action on the reservoir 100, which remains stationary relative to the body 10. In this primed position shown in FIGS. 4a, 4b, 5, 6, 7, and 8, the device is thus in its standby position.

When the user inhales through the mouthpiece 400, the deformable air chamber 60 deforms, and this causes the trigger element 600 that is fastened to said air chamber 60 to pivot. This movement of the trigger element 600 causes the latch 501 to pivot relative to the projection 59 of the actuator member 50, so as to release the blocking means 500. Under the effect of the spring 70, the cocking member 800 is thus moved axially upwards, and thus pushes the actuator member 50 axially upwards, as can be seen in FIGS. 9a to 24.

This axial movement of the cocking member 800 causes the meshing wheel 900 to turn. Since the cam projection 920 of said meshing wheel 900 is offset relative to the axis of rotation, in particular being arranged in the proximity of the periphery of said disk 930, it performs a circular movement while said meshing wheel is turning. FIGS. 7, 10, 15, 18, and 23 show in detail the position of said cam projection 920 respectively at the start of turning, after one-fourth of a turn, after half a turn, after three-fourths of a turn, and after a complete turn of said meshing wheel 900.

Since the cam projection 920 is arranged in the cam opening 1003 of said reservoir support element 1000, the circular movement of the cam projection 920 firstly moves said cam projection sideways in said cam opening 1003, as shown in detail in FIGS. 8, 11, 16, 19, and 24, and secondly entrains said reservoir support element 1000 in axial movement relative to the body 10, and thus relative to the valve member 210.

Said reservoir support element 1000 can move relative to said support plate 1100 only in translation, by the guide pins 1005 co-operating with the guide splines 1105. The co-operation between the holding elements 1104 and the holding ramps 1004 also ensures that said reservoir support element 1000 moves in translation only relative to said support plate 1100. Consequently, over the first half of the axial stroke of the cocking member 800, i.e. over the first half turn of the meshing wheel 900, the cam projection 920 moves said reservoir support element 1000, and thus said reservoir 100, axially upwards, and this actuates the valve 200. Over the second half of the axial stroke of the cocking member 800, i.e. over the second half turn of the meshing wheel 900, the cam projection 920 returns towards its start position and thus moves said reservoir support element 1000 together with said reservoir 100, axially downwards, and this returns the valve into its rest position.

Thus, a complete stroke of the cocking member 800, and thus a complete turn of the meshing wheel 900, corresponds to a complete actuation cycle of the valve 200, with reciprocating relative movement between the reservoir 100 and the valve member 210 of the valve 200.

Figure 21:
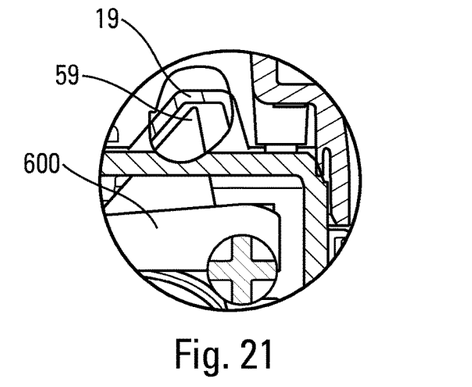
FIG. 21 is a view similar to the view in FIG. 13, in said triggered position, after the complete axial stroke of the slider.
Figure 22:
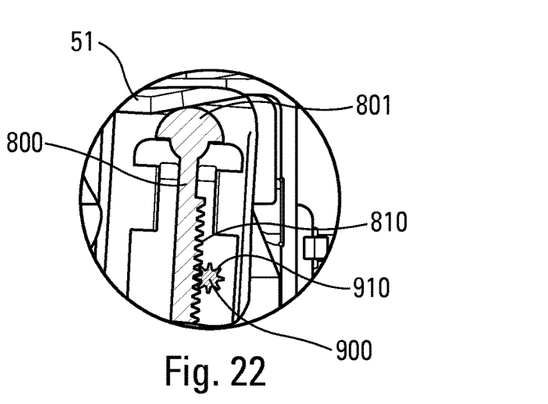
FIG. 22 is a view similar to the view in FIG. 14, in said triggered position, after the complete axial stroke of the slider.
Figure 23:
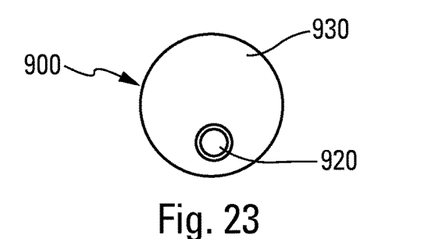
FIG. 23 is a view similar to the view in FIG. 18, in said triggered position, after the complete axial stroke of the slider.
Figure 24:
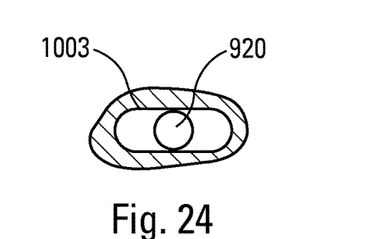
FIG. 24 is a view similar to the view in FIG. 19, in said triggered position, after the complete axial stroke of the slider.

The dispensing position of the cocking member 800, i.e. the end of its axial actuation stroke, is defined by an abutment between said projection 59 of the actuator member 50 and a portion 19 that is stationary relative to the body 10, as can be seen in FIG. 21.

At the end of inhaling, the user closes the cover elements 11, 12, and this returns the device into its rest position, ready for subsequent use.

The present invention is described above with reference to an advantageous embodiment, but naturally any modification could be applied thereto by a person skilled in the art, without going beyond the ambit of the present invention, as defined by the accompanying claims.

The invention claimed is:

1. A fluid dispenser device triggered by inhaling, comprising a fluid reservoir containing a fluid and a propellant gas, a metering valve being assembled on said reservoir for selectively dispensing the fluid, said device further comprising:
   a cocking member that is movable firstly between a rest position and a primed position by compressing a spring, and that is axially movable secondly between said primed position and a dispensing position under the effect of the force exerted by said compressed spring;
   blocking means for blocking said cocking member in said primed position; and
   a trigger system that is controlled by inhaling so as to release said blocking means;
   wherein said cocking member includes a set of teeth, and the device further comprises:
   a reservoir support element that is fastened to said reservoir and that includes a cam opening; and
   a meshing wheel rotatable about a meshing wheel axis extending in an axial direction and comprising a toothed projection that projects in the axial direction, wherein teeth of the toothed projection extend radially relative to the axial direction, and wherein the toothed projection is configured to co-operate with said set of teeth of said cocking member; the meshing wheel further comprising a cam projection that extends along an axis parallel to the axial direction and is configured to co-operate with said cam opening of said reservoir support element, said toothed projection being substantially centered relative to the meshing wheel axis, and said cam projection being radially offset relative to said meshing wheel axis, said meshing wheel co-operating with said cocking member so that when said cocking member moves from its primed position towards its dispensing position, said meshing wheel performs a complete turn, such that said cam projection performs a circular movement causing said reservoir support element to perform reciprocating axial movement, with a first axial movement for actuating said metering valve and a second axial movement in the opposite direction for returning the metering valve into the rest position.

2. The device according to claim 1, further comprising an actuator member that co-operates with said cocking member, said actuator member being provided with a cam surface for moving said cocking member from a rest position towards a primed position, said actuator member co-operating in said primed position with said blocking means so as to hold said cocking member in said primed position until inhalation, and said actuator member being moved by said cocking member towards a dispensing position after said blocking means have been released so as to actuate said valve.

3. The device according to claim 2, wherein said blocking means include a latch that, in its blocking position, co-operates with a projection of said actuator member.

4. The device according to claim 1, wherein said trigger system controlled by inhaling comprises a deformable air chamber that is deformed during inhaling, said deformable air chamber being fastened to a trigger element, such as a pivot rod.

5. The device according to claim 4, wherein said blocking means are secured to said trigger element.

6. The device according to claim 1, comprising a body containing the fluid reservoir and wherein said reservoir support element co-operates with a support plate that is secured to said body.

7. The device according to claim 6, wherein said support plate includes holding elements that are adapted to co-operate with holding ramps of said reservoir support element.

8. The device according to claim 6, wherein said support plate includes rectilinear guide splines that are adapted to co-operate with guide pins of said reservoir support element.

9. The device according to claim 1, wherein said toothed projection extends axially in a first direction and said cam projection extends axially in a second direction, opposition to said first direction.

\* \* \* \* \*